WATER-INSOLUBLE AZOMETHINE COMPOUNDS

This application is a continuation of copending application Ser. No. 653,119, filed Jan. 28, 1976, now abandoned, which application was a continuation-in-part of copending application Ser. No. 550,918, filed Feb. 19, 1975, now abandoned.

The present invention relates to new water-insoluble azomethine compounds of the general formula I

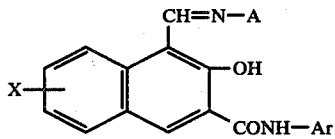

in which A stands for hydrogen, a radical of the benzene or naphthalene series or a heterocyclic radical, Ar stands for the naphthyl group or the phenyl group which groups may carry one to three substituents selected from the group consisting of lower alkyl, lower alkoxy, lower alkylsulfonyl, carboxy, lower carbalkoxy, trifluoromethyl, nitro, cyano, lower alkanoylamino, benzoylamino, carbonamido or sulfonamido groups and/or halogen atoms, preferably chlorine or bromine atoms; or for a benzimidazolene, chlorobenzimidazolone, tetrahydrodioxoquinazolone, tetrahydrodioxoquinoxaline, phthalimide or tetradydrodioxophthalazine radical, which heterocyclic groups may be further substituted, and X stands for a hydrogen, chlorine or bromine atom.

By "lower" there are to be understood groups being or containing alkyl groups of 1 to 4 carbon atoms.

This invention moreover relates to a process for the preparation of these compounds of formula I or mixtures thereof, which comprises condensing 1 mol of one or more aldehydes of the general formula II

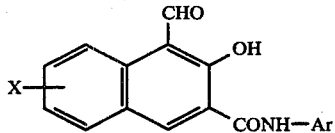

in which Ar and X are defined as above, with 1 mol of one or more amines of the general formula III

A — NH$_2$     (III)

in which A is defined as above.

As radicals Ar, there are mentioned, for example, phenyl, o-, m-, p-tolyl, o-, m-, p-methoxyphenyl, o-, m-, p-ethoxyphenyl, o-, m-, p-chlorophenyl, o-, m-, p-bromophenyl, o-, m-, p-nitrophenyl, 2,4-dimethylphenyl, 2,5-dimethoxyphenyl, 2,4-dichlorophenyl, 2,5-dichlorophenyl, 2,4,5-trichlorophenyl, 2-chloro-3-methylphenyl, 2-chloro-4-methylphenyl, 2-chloro-5-methylphenyl, 3-chloro-2methylphenyl, 4-chloro-2-methylphenyl, 2-methoxy-5-chlorophenyl, 2,5-dimethoxy-4-chlorophenyl, 2,4-dimethoxy-5-chlorophenyl, 2-methoxy-4-chloro-5-methylphenyl, 4-acetylaminophenyl, 4-benzoylaminophenyl, benzimidazolyl, phthalimidyl, tetrahydrodioxoquinoxalyl, tetrahydrodioxoquinazolyl or tetrahydrodioxophthalazinyl.

Preferred azamethine compounds are particularly those corresponding to the general formula IV

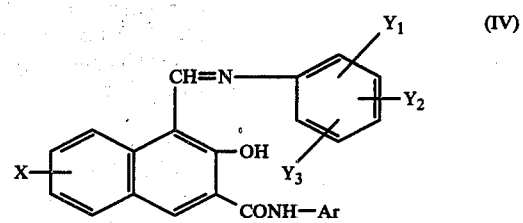

in which X and Ar are defined as above, and $Y_1, Y_2$ and $Y_3$ may be identical or different and stand for hydrogen or non ionic substituents.

As non ionic substituents, there are mentioned, for example, halogen atoms, especially chlorine or bromine atoms; alkyl groups, especially alkyl groups of 1 to 4 carbon atoms, preferably methyl or ethyl groups; alkoxy groups, especially having 1 to 4 carbon atoms, preferably methoxy and ethoxy groups; nitro groups; alkyl- or arylsulfonyl groups, especially alkylsulfonyl groups having 1 to 4carbon atoms in the alkyl moiety, phenyl, tolyl, sulfonamido-phenyl, carbon-amidophenyl-sulfonyl, or the N-methyl- or N-ethyl-substituted radicals thereof, carboxylic acid ester groups, optionally substituted sulfonic acid amide or carboxylic acid amide groups, or acylamino groups. Among the carboxylic acid esters groups, the carboxylic acid alkyl ester groups having 1 to 4 carbon atoms in the alkyl moiety are preferred, among optionally substituted sulfonic acid amide or carboxylic acid amide groups, those groups which carry one or two lower alkyl groups or a phenyl group which may again be substituted by non-ionic substituents, such as lower alkyl, lower alkoxy, carbonamide or sulfonamide groups and/or chlorine atoms, are preferred.

Acylamino groups are, in particular, lower alkanoylamino groups, such as acetyl- or propionylamino groups, and benzoyl or phenylsulfonylamino groups which carry one or more of the above-cited non ionic substituents, among them preferably a radical of the formula

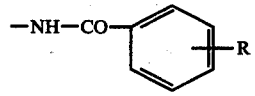

in which R stands for hydrogen, lower alkyl, lower alkoxy, a sulfonamide or carbonamide group or a chlorine atom.

Especially valuable properties are found in the new azamethine compounds, wherein at least one of the substituents $Y_1$, $Y_2$ or $Y_3$ contains a grouping of the formula —CO—NH— or wherein $Y_1$ and $Y_2$, taken together, stand for a grouping of the formula —NH—CO—NH—, —CO—NH—CO—, —NH—CO—NH—CO—, —NH—CO—CO—NH— or —CO—NH—NH—CO—.

As aromatic amines of formula III, there are especially mentioned amino-benzamides, amino-benzanilides, acylaminoanilines, amino-phenyl-sulfonamides, alkyl- or arylsulfonaminoanilines, amino-benzimidazoles, amino-benzoxazoles, amino-benzthiazoles, amino-phthalic acid imides, amino-quinazolinones, amino-quinoxalines, or amino-phthalazines, which are United States Patent [19]

Hunger

[11] 4,131,733
[45] Dec. 26, 1978

[54] WATER-INSOLUBLE AZOMETHINE COMPOUNDS

[75] Inventor: Klaus Hunger, Kelkheim, Fed. Rep. of Germany

[73] Assignee: Hoechst Aktiengesellschaft, Frankfurt am Main, Fed. Rep. of Germany

[21] Appl. No.: 827,380

[22] Filed: Aug. 24, 1977

Related U.S. Application Data

[63] Continuation of Ser. No. 653,119, Jan. 28, 1976, abandoned, which is a continuation-in-part of Ser. No. 550,918, Feb. 19, 1975, abandoned.

[30] Foreign Application Priority Data

Feb. 21, 1974 [DE] Fed. Rep. of Germany ....... 2408291

[51] Int. Cl.$^2$ ............................................. C09B 17/04
[52] U.S. Cl. .................................. 542/406; 542/420; 260/519; 260/559 S; 260/562 N; 562/440; 560/35
[58] Field of Search ................................ 542/420, 406

[56] References Cited

U.S. PATENT DOCUMENTS

| 3,875,200 | 4/1975 | L'Epplatlenier et al. ....... 260/439 R |
| 3,923,793 | 12/1974 | Mandlos et al. ..................... 542/442 |

*Primary Examiner*—Allen B. Curtis
*Attorney, Agent, or Firm*—Curtis, Morris & Safford

[57] ABSTRACT

Condensing of 1-formyl-2-hydroxy-3-naphthalenecarboxylic acid arylamides with ammonia or aromatic amines yields novel azamethines which are useful as coloring matters, especially as pigments.

10 Claims, No Drawings

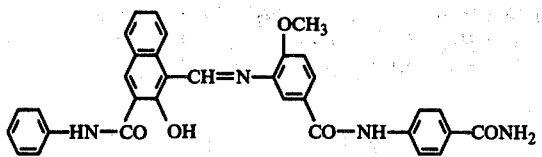

were obtained.

EXAMPLE 3

7.3 Grams of 2-hydroxy naphthalene-3-carboxylic acid anilide 1-aldehyde were dissolved at the boil in 300 ml of ethanol. A solution of 4.4 g of 5-aminobenzimidazolone in 100 ml of glacial acetic acid was added at 80° C, whereupon an intensely orange red colored pigment precipitated at once. Stirring was continued for 1 hour at 80° C, the mixture was allowed to cool to 20° C, suction-filtered, washed with methanol and water and dried.

Yield: 10 g of a pigment of the formula

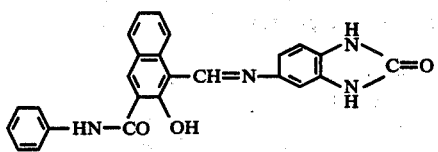

EXAMPLE 4

19.3 Grams of 2-hydroxy naphthalene-3-carboxylic acid-2',5'-dimethoxy-4'-chloroanilide 1-aldehyde were mixed in a high-speed stirrer with 200 ml of water and 100 ml of glacial acetic acid. While stirring, a solution of 12.5 g of 3-amino-4-methoxy-benz-anilide in 100 ml of dimethylformamide was added to this suspension. The temperature was maintained at 95° C for 10 hours, the product was then suction-filtered, washed with hot water and dried.

Yield: 23.7 g of a reddish yellow pigment of the formula

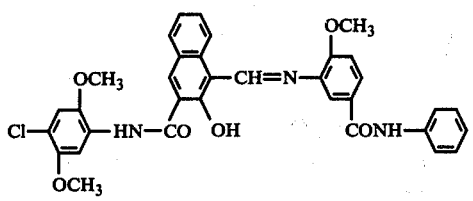

Upon incorporation into polyvinyl chloride the pigment thus obtained yielded a reddish yellow coloration having a very good purity, color intensity and fastness to migration and light.

EXAMPLE 5

38.6 Grams of 2-hydroxy naphthalene-3-carboxylic acid-2',5'-dimethoxy-4'-chloroanilide 1-aldehyde were dissolved at 120° C in 500 ml of dimethylformamide. Then, a solution of 19 g of 2-amino-4-acetylamino-anisole in 100 ml of water and 50 ml of glacial acetic acid were added dropwise. Stirring was continued for 3 hours at 100° C, the mixture was suction-filtered when cooled to room temperature, washed with water and dried.

Yield: 42.2 g of a reddish yellow pigment of the formula

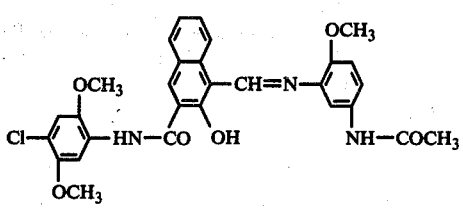

EXAMPLE 6

29.2 Grams of 2-hydroxy-naphthalene-3-carboxylic acid anilide 1-aldehyde were heated at the boil in 500 ml of glacial acetic acid and 500 ml of ethanol. To the hot suspension, a solution of 14 g of anthranilic acid in 50 ml of dimethylformamide was added, whereupon a clear solution was obtained, from which at once a reddish yellow pigment crystallized. The product was refluxed for 5 hours, cooled and suction-filtered at room temperature. It was washed with methanol and water and dried.

Yield: 38.5 g of a pigment of the formula

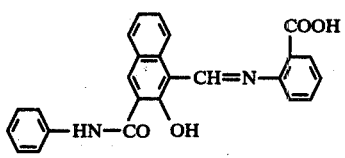

EXAMPLE 7

7.7 Grams of 2-hydroxy naphthalene-3-carboxylic acid-2'-methylanilide-1-aldehyde were dissolved at 80° C in 1000 ml of ethanol, and a solution of 4.6 g of 5-aminobenzimidazolone in 100 ml of glacial acetic acid was added thereto. The mixture was then refluxed for 2 hours. The orange-colored pigment was suction-filtered, washed with hot ethanol and water and dried.

Yield: 9.9 g of a pigment of the formula

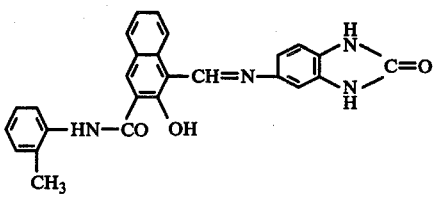

EXAMPLE 8

A solution of 31.4 g of 5-amino-2-benzoylamino-1,4-dimethoxybenzene in 200 ml of glacial acetic acid, 400 ml of water and 10 ml of a 10% solution of oxethylated stearyl alcohol was prepared. While stirring rapidly, a solution of 30.5 g of 2-hydroxy-3-carboxylic acid-2'-methylanilide-1-aldehyde is in 200 ml of dimethylformamide was added dropwise. Stirring was continued for 3 hours at 100° C, the reaction mixture was cooled and the product suction-filtered at room temperature. After washing with methanol and water and subsequent drying, 52.5 g of an intensely yellow colored pigment of the formula

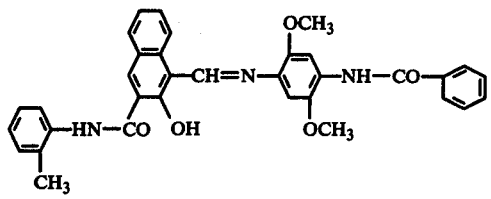

were obtained.

EXAMPLE 9

32.1 Grams of 2-hydroxy-3-carboxylic acid-2'-methoxy anilide 1-aldehyde were dissolved at 80° C in 300 ml of glacial acetic acid. This solution was combined with 10 ml of a 10% aqueous solution of oxethylated stearyl alcohol, and 27.7 g of 5-amino-2-benzoylamino-3-methyl-6-methoxy-benzene in 200 ml of glacial acetic acid and 300 ml of water were added. Stirring was continued for 3 hours at 100° C and, after the usual workup, 50.1 g of an intensely orange colored pigment of the formula

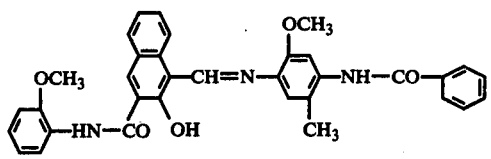

were obtained.

EXAMPLE 10

33.5 Grams of 2-hydroxy-3-carboxylic acid-2'-ethoxyanilide-1-aldehyde were dissolved at 70° C in 250 ml of dimethylformamide. This solution was added dropwise within 20 minutes to a solution of 31.4 g of 5-amino-2-benzoylamino-1,4-dimethoxybenzene in 200 ml of glacial acetic acid, 300 ml of water and 10 ml of a 10% aqueous solution of an oxethylated stearyl alcohol. The mixture was heated to 95° C and this temperature was maintained for 3 hours, the product was suction-filtered while hot, washed with hot water and dried. Yield: 51.2 g of a red azamethine pigment of the formula

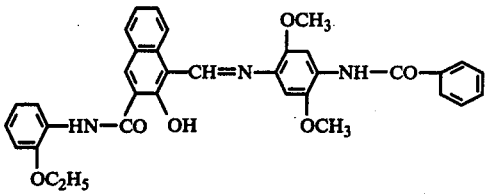

were obtained.

EXAMPLE 11

33.2 Grams of 2-hydroxy naphthalene-3-carboxylic acid-4'-acetylamino-anilide-1-aldehyde were heated at the boil in 350 ml of ethanol. Then 4 g of a concentrated aqueous ammonia solution in 30 ml of ethanol were added dropwise. Refluxing was continued for 60 minutes and, after the usual work-up, 32.7 g of a reddish yellow azamethine pigment of the formula

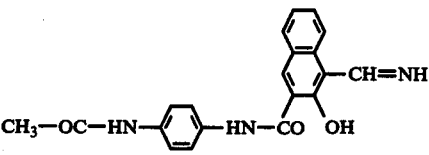

were obtained.

EXAMPLES 12 – 26

The following Table comprises further dyestuffs of the invention which can be prepared from amines of the formula III (A—$NH_2$) and 1-naphthaldehydes of the above formula II, according to the method disclosed in Examples 1 to 11:

TABLE

| Example | A—$NH_2$ | 1-naphthaldehyde(II) Ar | X | shade produced with azamethine pigment |
|---|---|---|---|---|
| 12 | $NH_3$ | 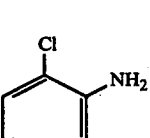 | Br | yellow |
| 13 | 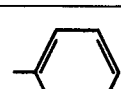 | 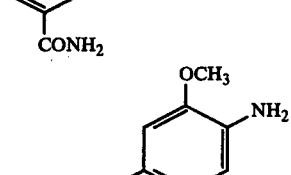 | H | reddish yellow |
| 14 | 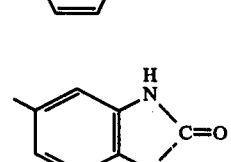 | benzimidazolone | H | red |

TABLE-continued
| Example | A—NH₂ | 1-naphthaldehyde(II) Ar | X | shade produced with azamethine pigment |
|---|---|---|---|---|
| 15 | 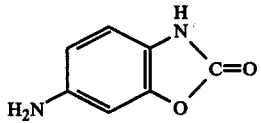 | 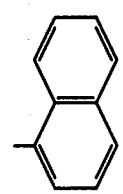 | H | yellowish red |
| 16 | 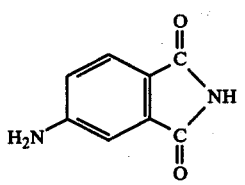 | 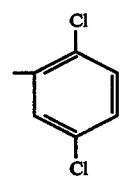 | H | reddish yellow |
| 17 | 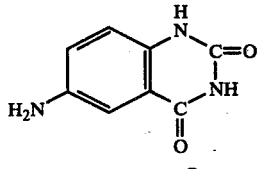 | 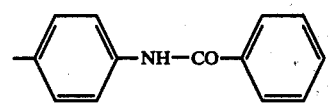 | H | yellowish red |
| 18 | 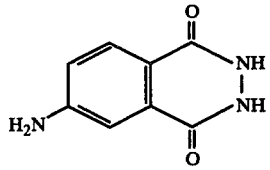 | 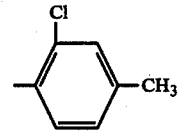 | H | yellowish red |
| 19 | 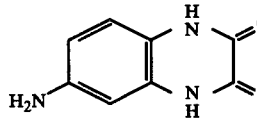 | 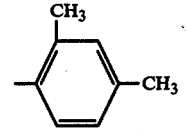 | H | yellowish red |
| 20 | 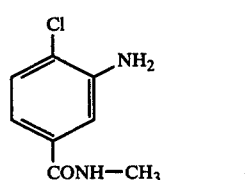 | 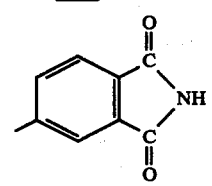 | H | orange |
| 21 | 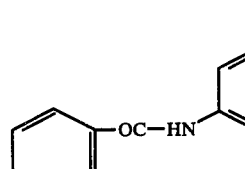 | 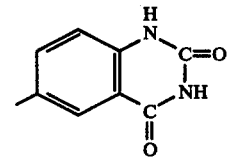 | H | yellowish red |
| 22 | 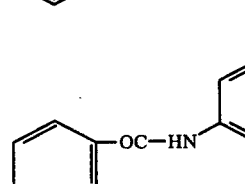 | 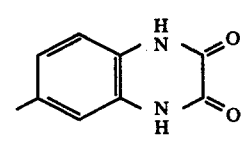 | H | red |
| 23 | 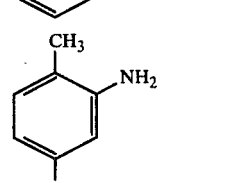 | 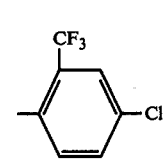 | H | yellow |

TABLE-continued

| Example | A—NH$_2$ | 1-naphthaldehyde(II) Ar | X | shade produced with azamethine pigment |
|---|---|---|---|---|
| 24 | 4-chloro-5-methyl-2-(acetylamino)aniline (2-amino-4-chloro-5-methyl-N-acetylaniline) | 4-ethoxyphenyl (—C$_6$H$_4$—OC$_2$H$_5$) | Br | reddish yellow |
| 25 | 5-amino-2,3-dihydro-1H-benzimidazol-2-one (5-aminobenzimidazolone) | 2-ethoxyphenyl (o-OC$_2$H$_5$—C$_6$H$_4$—) | H | yellowish orange |
| 26 | 5-amino-6-nitro-2,3-dihydro-1H-benzimidazol-2-one | 4-chlorophenyl (—C$_6$H$_4$—Cl) | H | yellowish red |

TABLE

| Example | A—NH$_2$ | 1-naphthaldehyde (II) Ar | X | shade |
|---|---|---|---|---|
| 27 | 5-aminobenzimidazolone | 2-chlorophenyl | H | yellowish orange |
| 28 | " | 2,4-dichlorophenyl | H | yellowish orange |
| 29 | " | 2-methoxy-3-chloro-4-methoxyphenyl (2,4-dimethoxy-3-chlorophenyl) | H | orange |
| 30 | 5-amino-6-nitrobenzimidazolone | 2,4-dimethoxy-3-chlorophenyl | H | yellowish red |
| 31 | " | 2,4-dichlorophenyl | H | yellowish red |
| 32 | 5-amino-6-chlorobenzimidazolone | 2,4-dichlorophenyl | H | reddish orange |
| 33 | 5-amino-6-ethoxybenzimidazolone | 2,4-dichlorophenyl | H | yellowish red |

TABLE-continued

| Example | A—NH₂ | 1-naphthaldehyde (II) Ar | X | shade |
|---|---|---|---|---|
| 34 | 4-Cl, 5-CH₃, 2-NHCOCH₃ aniline | phenyl | H | yellow |
| 35 | 2,5-di-OCH₃, 4-(C₆H₅O-CH-NH) aniline | phenyl | H | yellowish red |
| 36 | 2-NH₂, 4-(2,5-dichloroanilido)-benzoic acid methyl ester | 2-OCH₃, 4-Cl, 5-OCH₃ phenyl | H | yellowish orange |
| 37 | 2-OCH₃, 4-(C₆H₅CONH), 5-CH₃ aniline | 2-CH₃ phenyl | H | yellowish red |
| 38 | 2-OCH₃, 4-(C₆H₅CO—NH), 5-CH₃ aniline | phenyl | H | yellowish red |
| 39 | 5-amino-7-chloro-benzimidazolone | 2,3-dichlorophenyl | H | yellowish orange |

EXAMPLE 40

0.8 Gram of the pigment obtained according to Example 1, 2.4 g of alumina hydrate and 4.8 g of a letter printing varnish were mixed on a three-roller mill, and the mixture was triturated to yield a letter printing ink having a pigment content of 10% and producing yellow prints of high purity and color intensity.

Upon incorporation with a lacquer or a spinning solution, yellow colorations of good fastness to light and solvents were obtained.

EXAMPLE 41

67 Grams of polyvinyl chloride, 33 g of a platicizer composition consisting of a mixture of equal parts of dioctyl phthalate and dibutyl phthalate, 0.1 g of the pigment obtained according to Example 3, and 0.5 g of titanium dioxide were mixed for 15 minutes at 150° C in a roller mill to produce a foil with an orange-red coloration, which was distinguished by a high intensity, pure shade and good fastness to light and migration.

EXAMPLE 42

4.5 Grams of the pigment obtained according to Example 5 were shaken for 45 minutes in a vibration ball mill with 25.5 g of a lacquer consisting of a 20% solution of alkyd resin in xylene, then 60 g of a clear varnish consisting of 52.5 parts by weight of a 70% alkyd resin solution in xylene, 35 parts by weight of a 55% melamine resin solution in butanol, 2.5 parts by weight of butyl glycol, 5 parts by weight of butanol and 5 parts by weight of white spirit were added.

A reddish yellow colored full shade lacquer was obtained, it was sprayed onto an aluminum sheet and stoved for 30 minutes at 140° C. The reddish yellow coloration thus obtained had a satisfactory fastness to overlacquering and a good fastness to light and weathering.

EXAMPLE 43

0.8 Gram of the pigment obtained according to Example 7 were processed as in Example 27 to yield a

I claim:
1. A compound of the formula

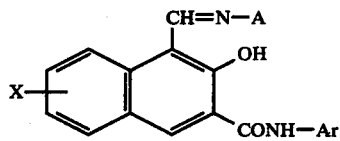

wherein X is hydrogen, chlorine or bromine, Ar is phenyl or naphthyl which are unsubstituted or substituted by 1 to 3 substituents selected from the group consisting of halogen; lower alkyl; lower alkoxy; trifluoromethyl; nitro; cyano; carboxy; lower carbo-alkoxy; lower alkyl sulfonyl; carbamoyl; sulfamoyl; carboxylic or sulfonic acid mono- or di-(lower alkyl)amide; carboxylic or sulfonic acid anilide which are unsubstituted in the phenyl nucleus or substituted by halogen, lower alkyl, lower alkoxy, cyano, carbamoyl or sulfamoyl; lower alkanoyl amino; phenyl sulfonyl or benzoyl amino which are unsubstituted in the phenyl nucleus or substituted by halogen, lower alkyl, lower alkoxy, cyano or nitro; or two substituents on Ar being phenyl together stand for a fused saturated 5- or 6-membered ring consisting of two adjacent carbon atoms of the phenyl nucleus and further ring members selected from the group consisting of —CO—, —NH—, —O— and —S—; and A is benzimidazolonyl-(2) which is unsubstituted or substituted by chlorine, methyl, methoxy, ethoxy, or nitro.

2. A compound as defined in claim 1, wherein Ar is naphthyl; phenyl; phenyl substituted by 1 to 3 substituents selected from the group consisting of chlorine, bromine, lower alkyl, lower alkoxy, trifluoromethyl, carboxy, nitro, lower carboalkoxy, lower alkanoylamino, benzoylamino, carbamoyl, sulfamoyl, carboxylic or sulfonic acid mono- or di-(lower alkyl)-amide, and carboxylic or sulfonic acid anilide which are unsubstituted or substituted in the phenyl nucleus by lower alkyl, lower alkoxy, chlorine or carbamoyl; phthalimidyl, benzimidazolonyl, benzoxazolonyl, tetrahydrodioxoquinazolonyl, tetrahydrodioxoquinoxazolyl or tetrahydrodioxophthalazinyl; which heterocyclic radicals are unsubstituted or substituted in the benzo nucleus by chlorine, bromine, lower alkyl, lower alkoxy or nitro.

3. A compound as defined in claim 1, wherein X is hydrogen and Ar is phenyl substituted by 1 to 3 substituents selected from the group consisting of chlorine, methyl, methoxy and ethoxy.

4. A compound as defined in claim 1, wherein X is hydrogen and Ar is phenyl, chlorophenyl, dichlorophenyl, tolyl, anisyl, ethoxyphenyl or dimethoxy chlorophenyl.

5. A compound of the formula

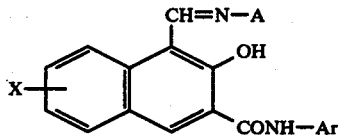

wherein X is hydrogen, Ar is phenyl, chlorophenyl, dichlorophenyl, tolyl, anisyl, ethoxyphenyl or dimethoxy chlorophenyl; and A is benzimidazolonyl-(2) which is unsubstituted or substituted by chlorine, methyl, methoxy, ethoxy, or nitro.

6. The compound as defined in claim 5, wherein A is 6-nitrobenzimidazol-2-on-5-yl and Ar is p-chlorophenyl.

7. The compound as defined in claim 5, wherein A is benzimidazol-2-on-5- yl and Ar is o-chlorophenyl.

8. The compound as defined in claim 5, wherein A is 6-chlorobenzimidazol-2-on-5-yl and Ar is 2,5-dichlorophenyl.

9. The compound as defined in claim 5, wherein A is 6-ethoxybenzimidazol-2-on-5-yl and Ar is 2,5-dichlorophenyl.

10. The compound as defined in claim 5, wherein A is benzimidazol-2-on-5-yl and Ar is o-toluidino.

* * * * *